United States Patent [19]

Buck et al.

[11] Patent Number: 4,688,021

[45] Date of Patent: Aug. 18, 1987

[54] COMBINED SMOKE AND GAS DETECTION APPARATUS

[75] Inventors: Robert H. Buck; Kent G. Cowan; John P. Doughty, all of Midland; Stephen E. Marshall, Lubbock, all of Tex.

[73] Assignee: BDC Electronics, Midland, Tex.

[21] Appl. No.: 838,469

[22] Filed: Mar. 11, 1986

[51] Int. Cl.⁴ .................... G08B 19/00; G08B 17/10
[52] U.S. Cl. ........................... 340/521; 340/522; 340/511; 340/628; 340/632; 340/691; 340/692; 340/384 E; 340/870.16
[58] Field of Search ........... 340/521, 506, 527, 870.16, 340/628–630, 632–634, 511, 510, 522, 691, 692, 384 E; 73/23, 23.1, 25, 27 A

[56] References Cited

U.S. PATENT DOCUMENTS 3,860,919  1/1975  Aker .................... 340/634
4,064,507 12/1977  Schmitz ................ 340/521
4,443,791  4/1984  Rissin et al. .......... 340/634
4,526,028  7/1985  Hübner ................. 340/632
4,586,143  4/1986  Kaneyasu et al. ....... 340/634

Primary Examiner—Donnie L. Crosland
Attorney, Agent, or Firm—Jerry W. Mills; Gregory M. Howison

[57] ABSTRACT

A combined smoke and gas detector utilizes a conventional smoke detector IC (44) which is operable to drive a piezo element (46) and an LED (94) to provide indication of a smoke or gas detection. An ionization chamber (58) is operable to detect smoke and a gas detector (98) is operable to detect gas. A comparator (104) detects the output of the gas detector (98) for input to the logic circuitry of the IC (44). The LED (94) is modulated to provide a distinction between gas detection and smoke detection in addition to the tone output from the piezo element (46).

3 Claims, 2 Drawing Figures

COMBINED SMOKE AND GAS DETECTION APPARATUS

TECHNICAL FIELD OF THE INVENTION

The present invention pertains in general to smoke and gas detectors and, more particularly, to a combined smoke and gas detector which allows multiplexing of alarm operations.

BACKGROUND OF THE INVENTION

Smoke detectors and gas detectors have been utilized separately for a number of years. However, until recently, circuitry required for these devices was rather complicated and did not lend itself to low cost consumer use. As a result of increasing market demand, integrated circuits have been developed which integrate a number of functions for smoke alarms onto a single chip. However, certain testing agencies such as Underwriters Labs have put certain restraints on smoke detectors which require certain output functions in order to operate.

When combining a smoke detector with a gas detector, it is still important to reduce the circuitry required for the combined operation of the system. At this point in time, smoke detectors and gas detectors are not commonly found together in an integrated unit. To integrate the functions of two separate devices into a single package would be expensive and difficult to manufacture. Therefore, there exists a need for an integrated smoke and gas detector which combines the output detection and alarm circuitry for both detection modes to reduce the overall amount of circuitry required for operation of the device.

SUMMARY OF THE INVENTION

The present invention disclosed and claimed herein comprises a combined smoke and gas detector. The detector includes a smoke sensor for generating a smoke level signal and a gas sensor for generating a gas level signal. A smoke detector compares the smoke level with a predetermined smoke threshold and outputs a smoke present signal when the smoke level exceeds the smoke threshold. A gas detector is provided for comparing the gas level with a predetermined gas threshold and outputting a gas present signal when the gas level signal exceeds the gas smoke threshold. Visual and audio output devices are providing a plurality of distinguishable audio and visual output signals. They are controlled in response to receiving the smoke and gas present signals by modulating the audio and visual output signals for each combination of the smoke and gas present signals.

In an alternate embodiment of the present invention, the delay circuit is providing for disabling the gas detection circuit during turn on. In addition, a reset button is provided for also disabling the output of a gas detector for a predetermined duration of time to allow the user to determine if noise gases are present.

BRIEF DESCRIPTION OF THE DRAWING

For a more complete understanding of the present invention and the advantages thereof, reference is now made to the following description taken in conjunction with the accompanying Drawings in which.

DETAILED DESCRIPTION OF THE INVENTION

Figure 1:
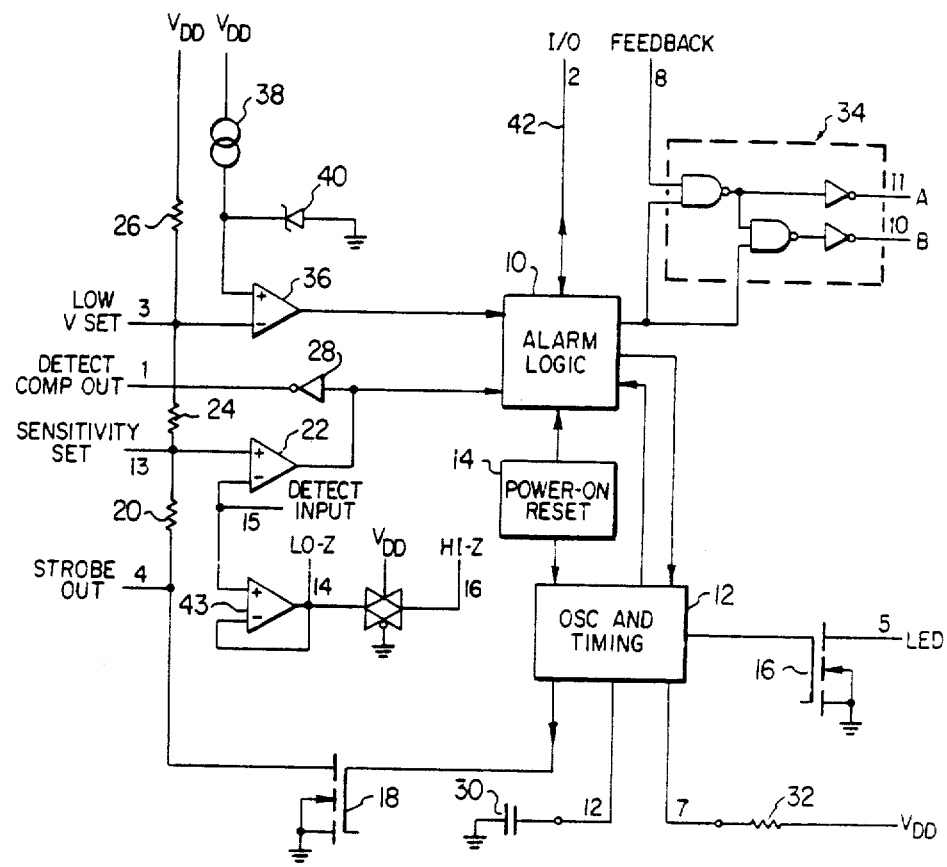
FIG. 1 illustrates a schematic diagram of a conventional smoke alarm integrated circuit.

The present invention utilizes a conventional smoke detector integrated circuit which has incorporated therein alarm logic, detection circuits and low battery circuits. The integrated circuit utilized in the preferred embodiment is of the type MC14468 manufactured by Motorola. A block diagram of this integrated circuit is illustrated in FIG. 1. However, it should be understood that any type of smoke detector integrated circuit with similar operating functions can be utilized. The smoke detector chips available in the industry typically comply with Underwriter Laboratories specification UL217 and, therefore, are generally compatible with some minor circuit variations external to the chip.

Referring further to FIG. 1, the smoke detector chip includes an alarm logic circuit 10 which interfaces with an oscillator and timing circuit 12. A power on reset circuit 14 is disposed between the alarm logic 10 and the oscillator and timing circuit 12. The oscillator and timing circuit 12 drives a transistor 16 which is operable to drive an external light emitting diode (LED). The oscillator also drives an internal transistor 18 at a predetermined frequency to provide a time base for other operation in this circuit.

The transistor 18 provides a source to drain path to ground for a strobe out signal. In addition, the output of the transistor 18 is connected through a resistor 20 to the positive input of a detect comparator 22 which has the negative input thereof connected to a detect input pin. The positive input of the comparator 22 is also connected through a resistor 24 to a low voltage set pin which is turn connected to $V_{DD}$ through a resistor 26.

The output of detect comparator 22 is connected to the input of alarm logic 10 and also to a detect output through a buffer 28. The positive input of the detect comparator 22 is connected to an ionization chamber utilized to detect smoke, as will be described hereinbelow. The oscillator and timing circuit 12 is controlled by an external timing capacitor 30 and connected from the oscillator to ground and also an external resistor 32 connected between the oscillator and timing circuit 12 and $V_{DD}$. The alarm logic circuit 10 is connected through a logic circuit 34 to provide a driven output for a piezo electric transducer (not shown).

In addition to the other logic on the chip, a low battery comparator 36 is provided which has the positive input thereof connected to the output of a current source 38 connected to $V_{DD}$. A zener diode 40 provides a reference level. The negative input of the comparator 36 is connected to the low voltage set input which can either "float" or be connected to an external reference. The low voltage battery detect circuit provides a capability to determine if a battery connected to $V_{DD}$ is below a predetermined threshold. The comparator 36 is output to the alarm logic circuit 10.

In operation, the internal oscillator 12 operates within a period of 1.67 seconds during no smoke conditions. Each 1.67 seconds, internal power is applied to the entire IC and a check is made for smoke. Every twenty four clock cycles, a check is made for low battery by comparing $V_{DD}$ to the reference voltage zener 40.

If smoke is detected, the oscillator period becomes 40 milliseconds and the piezo electric horn oscillator circuit 34 is modulated to an ON condition for 160 milliseconds and to an OFF condition for 80 milliseconds. During the OFF time, smoke is again checked and will inhibit further horn output if no smoke is sensed. During the local smoke conditions, the low battery alarm is inhibited, but the LED is pulsed at a 1.0 hertz rate. The circuit of FIG. 1 provides for remote sensing of circuit on an I/O pin 42 which allows a detect output to be provided to other smoke detectors or for the signals to be received from other smoke detectors that they have been set. Whenever a local alarm is sounded, the LED connected to the transistor 16 is pulsed. However, when a remote smoke detector triggers, the LED is inhibited.

An active guard is provided to surround the ionization chamber. This is provided with a guard amp 44 which has the negative input thereof connected to the output and the positive input connected to the detect input pin. A high and low impedance pin are provided and are operable to be disposed adjacent the detect input. The voltage on these pins will be within 100 millivolts of the input signal. This will keep surface leakage currents to a minimum and provide a method of measuring the input voltage without loading the ionization chamber. The active guard amplifier 43 is not strobed and thus gives constant protection from surface leakage currents.

The smoke detector circuit of FIG. 1 also provides the capability to bypass the power strobe unit. This is provided by forcing the timing input of the oscillator and timing circuit 12 to which the capacitor 30 is connected to a low voltage, the power strobing is bypassed and the output constantly shows smoke/no smoke condition.

Figure 2:
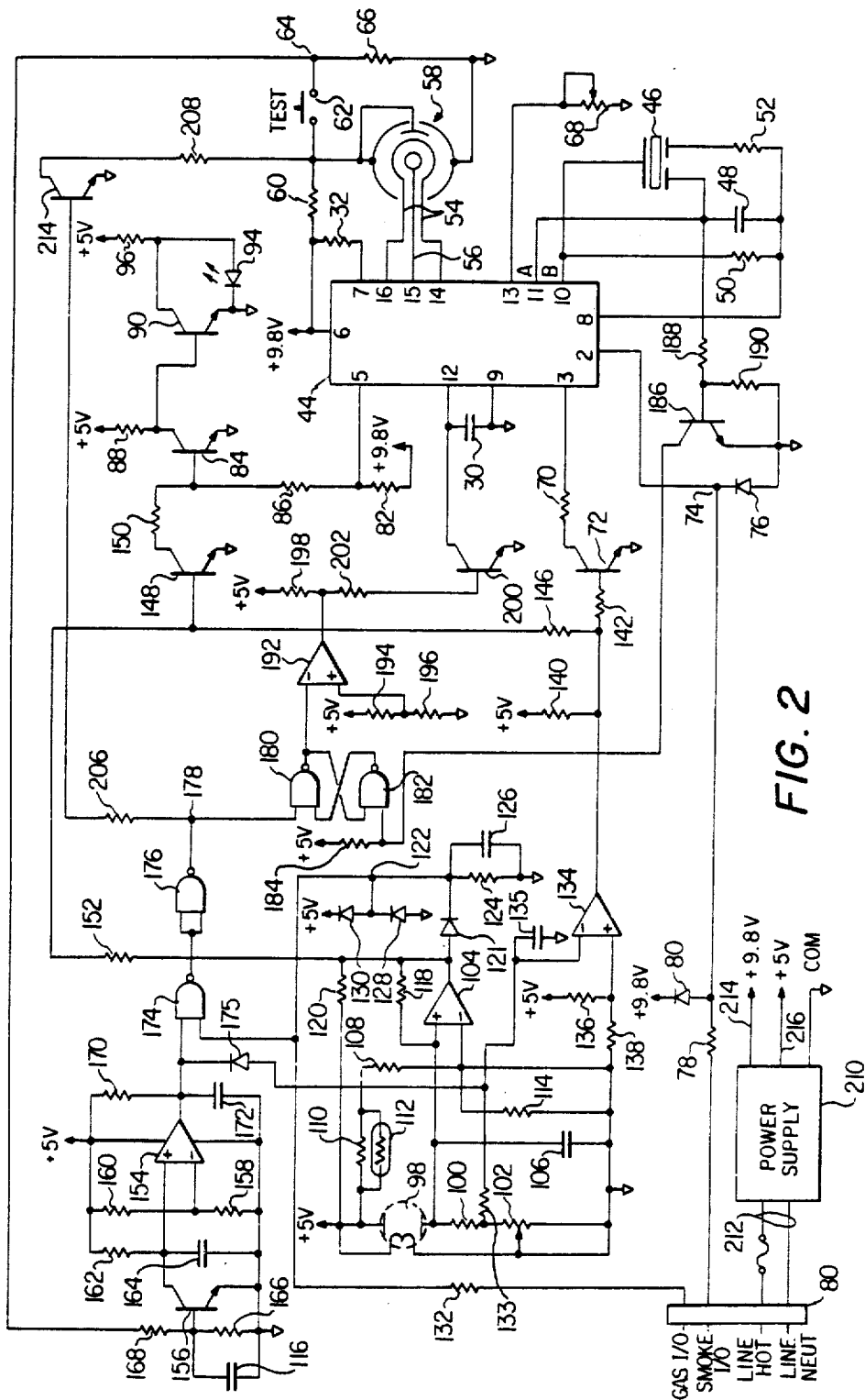
FIG. 2 illustrates a schematic diagram of the combined smoke and gas detector.

Referring now to FIG. 2, there is illustrated a schematic diagram of the combined smoke and gas detector of the present invention utilizing the circuit of FIG. 1 in which it is generally referred to by the reference numeral 43. The two driver outputs from the IC 44 are connected across a piezo electric element 46 of the type PKM29-3A, manufactured by Murata. One output is referred to as the A-output and the other output is referred as the B-output. The A-output is connected to the feedback input "F" through a capacitor 48 and the B output is connected to a resistor 50 to the F input. A resistor 52 is provided for connection between the piezo electric element 46 and the F-input. A connection for this IC 44 is further illustrated in the Motorola specification sheet for the MC14468 integrated circuit beginning at page 8-13.

The guard outputs of the guard amp 43 are connected to leads 54 which are disposed on either side of a lead 56. The lead 56 goes to an ionization chamber 58 of the type DCS-A3, manufactured by Amersham. The ionization chamber 58 has a high input and a low input, the low input being connected to ground and the high input being connected to the positive battery voltage through a resistor 60. The high node of the ionization chamber 58 is also connected through a test switch 62 to a node 64, the node 64 being connected to ground through a resistor 66.

The sensitivity input for the detector is connected through a potentiometer 68 to ground, the potentiometer 68 providing a sensitivity setting therefor. The low voltage set input is connected to ground through a series connected resistor 70 and NPN transistor 72. The NPN transistor 72 is operable, when conducting, to place the resistor 70 in parallel with the low voltage set input to low voltage thereof, the operation of which will be described hereinbelow. The I/O pin is connected to a node 74 which is connected to the cathode of a diode 76, the anode of which is connected to ground. The node 74 is connected through a resistor 78 to a smoke I/O on an interface connector 80. In addition, the node 74 is connected to the anode of a diode 81, the cathode of which is connected to a positive voltage.

The LED output is connected to 9.8 V through a resistor 82 and also to the base of a transistor 84 through a resistor 86. The transistor 84 has the collector thereof connected to a positive voltage through a resistor 88 and also the base of an NPN transistor 90. The transistor 90 has the emitter thereof connected to ground and the collector thereof connected to the anode of a diode 94, the cathode of which is connected to ground. The collector of transistor 90 is also connected to a positive voltage through a resistor 96. When the LED input is pulsed, the transistor 84 is modulated, thus modulating transistor 90.

A gas detector 98 of the type TGS813P, manufactured by Figaro, has the positive input thereof connected to +5 volts and the negative input thereof connected through a first resistor 100 and a potentiometer 102 to ground. The gas detector 98 has a heater element which has one end thereof connected to ground and the other end thereof connected to the +5 volts. The voltage output is detected across the gas detector 98 with a comparator 104. The positive input of the comparator 104 is connected to the negative input of the gas detector 98 with a capacitor 106 connected from the positive to ground. The negative input of comparator 104 is connected through a first resistor 108 connected in series with a second resistor 110 to the positive voltage supply. The resistor 110 has a thermister 112 disposed there across for temperature compensation purposes. The comparator 104 also has the negative input thereof connected to ground through a parallel configured resistor 114. The positive input thereof is connected to the output through a feedback resistor 118.

The output of the comparator 104 is connected to a pull up resistor 120 to the positive voltage supply and also to a node 122 through a diode 121. The node 122 has a parallel configured resistor and capacitor 124 and 126, respectively, connected to ground and also a series diode pair having one diode 128 reversed biased and connected to ground and a second diode 130 reversed biased and connected to a positive voltage supply from the node 122. The node 122 is connected to the output connector 80 through a resistor 132 to the "gas I/O" line.

A second comparator 134 is provided having the negative input thereof connected through a resistor 133 to the midpoint of resistor 100 and potentiometer 102, thus providing a connection to the negative output of the gas detector 98. A capacitor 135 is connected between the negative input of comparator 134 and ground. The positive input of comparator 134 is connected to a voltage divider comprised of a first resistor 136 connected to a positive voltage and a second resistor 138 connected to ground. The output of the comparator 134 is connected to a pull up resistor 140 to a positive voltage and through a resistor 142 to the basic transistor 72. The transistor 72, described above, is operable to place the resistor 70 in parallel with the low voltage setting on the input of the IC 44. In effect, this forces the IC 44 into a state that simulates a low voltage condition.

The output of comparator 134 is also connected through a resistor 146 to the base of a transistor 148, the emitter of which is connected to ground and the collector of which is connected to the base of the transistor 84 through a resistor 150. When transistor 148 is turned on, this effectively grounds the base of transistor 84 regardless of the LED output on the IC 44 since the resistor 86 is approximately 100 times larger than resistor 150. The base of transistor 148 is also connected to the output of the first comparator 104 through a resistor 152. Therefore, both comparators 104 and 134 are operable to control the operation of the LED 94 and override the control thereof by the IC 44.

A delay circuit is provided for delaying operation of the gas detector 98 upon warm up of the gas and smoke detector. The delay device is comprised of a comparator 154 which has the positive input thereof connected to the collector of a transistor 156 and the negative input thereof connected to ground through a resistor 158. The negative input is also connected to the positive supply volts through a resistor 160 and positive input thereof is also connected to a positive voltage through a resistor 162. A capacitor 164 is provided across the positive input and ground with the emitter of the transistor 156 connected to ground also. The base of transistor 156 is connected to a voltage divider comprised of a first resistor 166 connected to ground and a second resistor 168 connected to node 64. A capacitor 116 is connected across resistor 166. The test switch 62 therefore raises the basic transistor 156 to a high voltage. The capacitor 164 and resistor 162 provide a RC time constant that is sufficiently long (approximately one minute) to hold the positive input of comparator 154 low with respect to the negative input thereof. This in turn causes the output to be low. The output of comparator 154 is connected to a pull up resistor 170 to the positive voltage and coupled through a capacitor 172 to ground. The output of comparator 154 is also connected to one input of a NAND gate 174, the other input of which is connected to node 122. The output of NAND gate 174 is connected to both inputs of a NAND gate 176, the output of which is connected to a node 178. The node 178 is held low by the delay circuit for approximately one minute after turn on and maintained at that level. The node 178 goes high after the delay and when the positive input of comparator 154 goes high. Thereafter, node 178 is only taken to a high voltage when the output of comparator 104 goes high which represents a condition where gas has been detected.

The output of comparator 154 is connected to the cathode of a diode 175, the anode of which is connected to the negative input of comparator 134. When the output of comparator 154 goes low, the output of comparator 134 goes high which simulates a low voltage condition.

The node 178 is connected to one input of latch circuit which is comprised of a NAND gate 180 and a NAND gate 182. NAND gate 180 has the output thereof connected to one input of NAND gate 182 and NAND gate 182 has the output thereof connected to one input of NAND gate 180. The other input of NAND gate 180 is connected to node 178 and the other input of NAND gate 182 is connected to a positive voltage through a resistor 184 and also to ground through an NPN transistor 186, the base of which is connected through a series resistor to the A-output of IC 44 through a resistor 188 and also to ground through a resistor 190. Transistor 186 is operable to drive the other input of NAND gate 182 with the voltage on the output of the A-output of IC 44.

The output of NAND gate 180 is also input to the negative input of a comparator 192, the positive input of which is connected to a voltage divider comprised of a resistor 194 connected to a positive voltage and a resistor 196 connected to ground. The output of comparator 192 has a pull up resistor 198 connected to a positive voltage and also to the base of a transistor 200 through a resistor 202. Transistor 200 has the emitter thereof connected to ground and the collector thereof connected to the oscillator input of IC 44 on the positive side of capacitor 30. Transistor 200 is operable to cause the internal oscillator in timing circuit 12 of IC 44 to go to a constant oscillation rather than the gated oscillation in the normal smoke detect mode. This occurs whenever the output of NAND gate 180 is low.

In node 178 on the output of NAND gate 176 is also connected to the base of a transistor 204 through a resistor 206. Transistor 204 has the emitter thereof connected to ground and the collector thereof connected through a resistor 208 to the positive side of the ionization chamber 58.

A power supply section 210 is provided which receives the line voltage on two lines 212 to output a first DC voltage on line 214 and a second DC voltage on lines 216. The first voltage is approximately 9.8 volts for driving the IC 44 and a second voltage on line 216 is approximately 5.0 volts for driving the logic circuitry.

In operation, there are a number of modes which must be distinguished between by the use of the LED 94 and the piezo electric crystal 46. The LED 94 is either blinking, ON or OFF and the crystal 46 is either cycled ON/OFF, constant or chirped. The alarm modes are illustrated in the following table.

| ALARM CONDITION | LED | BUZZER |
|---|---|---|
| Smoke (Origin) | Blink | On/Off |
| Smoke (Remote) | On | On/Off |
| Gas (Origin) | Off | Constant |
| Gas (Remote) | On | Constant |
| Low Battery | On | Chirp |
| Trouble Alarm | Off | Chirp |
| Reset (gas/smoke) | Off | Chirp |

A first mode is the smoke detecting mode both local and remote, a second mode is the gas detecting mode both local and remote and a third mode is a trouble mode for indicating that either the gas sensor 98 has a problem or there is a low battery condition. Each of these modes is distinguished with only the LED 94 and the piezo element 46. By multiplexing the operation of the IC 44 with the various circuitry described above, a number of different modes can be differentiated between. In addition, it is necessary to differentiate between remote units in a loop of smoke and gas detectors, as will be described hereinbelow.

In the smoke sensing mode, the ionization chamber 58 outputs a signal on the line 56 to the IC 44. This causes the IC 44 to go into the normal OR mode. In this mode, the piezo crystal is activated at a frequency of approximately 1.2 kilohertz which frequency is gated about every quarter of a second. This provides a distinctive tone. In addition, the LED 94 is modulated. In normal operation with no smoke detected, the LED 94 is on to indicate power. To maintain the LED 94 on, transistor 84 is maintained OFF by the voltage on the LED output of IC 44 being maintained low. In addition, transistor 148 is maintained off. When smoke is detected and the IC 44 goes into the alarm mode, the LED output goes high momentarily to turn transistor 84 on and subsequently turn transistor 90 off. This provides a "blinking" LED.

When a number of smoke detectors are arranged in a "loop", smoke detection is followed by activation of all of the piezo elements and all of the detectors in the various remote locations. This is facilitated by a signal which is output from the I/O port of the IC 44 through resistor 78 to the connector 80. The internal logic circuitry of the IC 44 causes the LED 94 to blink only at the location at which the associated ionization chamber 58 indicated a smoke alarm condition. The remaining units have an LED that is constantly on. By examining the LEDs in the various locations, the detector that actually detected the smoke can be distinguished.

In the gas detection mode, comparator 104 senses the voltage and the positive input thereof goes low and the output thereof goes high, resulting in a high voltage on node 122. This causes a high voltage on node 178 which turns on transistor 214 and places the resistor 208 in parallel with the ionization chamber 58. This causes the IC 44 to enter the alarm state and activate the piezo element 46. At this point, the operation is similar to that in the smoke alarm condition.

To distinguish between the smoke alarm condition and the gas alarm condition, the piezo element 46 is maintained constantly on to provide a distinguishing frequency. To facilitate this, the voltage on node 178 is input to the latch circuit comprised of the NAND gate 180 and 182 for changing the output state of comparator 192 to a high logic state to turn on transistor 200 and bypass capacitor 30. This effectively removes the gating of the internal oscillator and provides a constant tone on the piezo element 46. However, it is necessary that the gating oscillator internal for the IC 44 be deactivated on the positive going edge of operation. To facilitate this, transistor 186 senses the leading edge and controls the latch on the input of NAND gate 182 to change the state of comparator 192 when the voltage on the A-output of IC 44 is high.

To provide another distinguishing parameter for gas detection, the output of comparator 104 in the gas detect mode controls transistor 148 to turn off transistor 84 which in turn turns on transistor 90 and turns off the LED 94. As described above, in the smoke detection mode, the LED will blink but, in the gas detection mode, the LED is constantly off.

In order to distinguish between gas detection at remote locations, the LED is turned completely off only at the location that the gas is actually sensed. At the remaining locations, the piezo element 46 and LED 94 is maintained constantly on. This is facilitated by the diode 121 which prevents a signal coming in on the gas I/O line on the connector 80 from controlling transistor 148. Transistor 148 can only be controlled when the detect signal is generated at the associated gas sensor 98.

A trouble condition on the gas sensor 98 can exist when, for example, the heater element internal thereto is defective. In this mode, the voltage on the negative side at the top of resistor 100 will go low. This will not trigger comparator 104 but, rather, will trigger comparator 134. This causes transistor 72 to turn on and also transistor 148. When transistor 72 turns on, as described above, this causes the IC 44 to go into the low battery condition. In the low battery condition, the piezo element 46 is controlled to chirp every minute and the LED is on. However, by turning transistor 148 on, the LED 94 is turned off. Therefore, a trouble condition is indicated by the LED being off and the low battery chirping signal from the piezo element 46 being present. If a battery system is utilized, a trouble condition can be distinguished from a low battery condition in that the LED will be on with the chirping signal for a low battery condition.

In order to test the system, the test switch 62 is provided for placing resistor 66 across the ionization chamber 58. In addition, depression of the test button 62 charges up capacitor 116 and turns on transistor 156 in the delay circuit to discharge capacitor 164 to change the voltage on the input of comparator 154 to a low state. The capacitor 116 requires approximately three to five seconds to discharge, thus requiring the test switch 62 to be depressed for this amount of time. In operation, there are two modes the test switch 62 is utilized for. The first mode is to test the ionization chamber 58. It is only necessary in this mode to depress the test button 62 for approximately one second or less until an audible response is received. In the second operation, the test switch 62 is utilized to discharge capacitor 116 to lower the voltage on the output of comparator 154 to lower the voltage on node 178 regardless of the voltage on node 122. This causes the output of NAND gate 180 to go high, thus lowering the voltage on the output of comparator 192 and turning off transistor 200. This is effectively reset for the latch comprised of NAND gates 180 and 182, as well as transistor 214. In the second mode, the reset function is primarily utilized to test the gas sensor 98.

In operation, it is necessary to have this reset function since some noise gases can be present to activate the gas sensor 98. When the unit alarms indicating that gas is present, it is only necessary to press the test button 62 for about three seconds and then release it. This causes the capacitor 116 to charge up, turning on transistor 156 to pull the positive input of comparator 154 to ground. This results in the output of comparator 154 going low which in turn causes the output of NAND gate 176 to go low, turning off transistor 214. When transistor 214 is turned back on, after the delay period set by capacitor 164 and resistor 162, the unit will again be in the alarm condition only if gas is still present. Since most gases like carbon monoxide cannot be detected by the individual, it is necessary to have this function. During the delay period, the IC 44 enters the low voltage mode and causes the crystal 46 to chirp once ever second, thus providing audible feedback.

In summary, smoke detection is indicated by a gated piezo element which provides a distinctive tone in addition to a blinking LED with the normal power condition of the LED being constantly on. Gas detection is indicated by the piezo element having a constant tone output and the LED being off. A trouble condition is indicated by a periodic chirp every minute with the LED being maintained off. A low battery condition is indicated by a periodic chirp every minute and the LED on. To distinguish between smoke detected locally and at remote locations, the local LED blinks and the remote LEDs are maintained constantly on. To distinguish between gas detection in a remote unit as opposed to a local location, the local location has the LED turned off and the remote locations have the LEDs maintained on with the distinguishing constant tone of the piezo element distinguishing over the gated tone for the smoke detection. By utilizing the circuit of the present invention, the functions of the smoke detector circuit are multiplexed to minimize the circuitry utilized in order to facilitate gas detection and smoke detection with the alarm logic circuitry in the smoke detector IC 44.

Although the preferred embodiment has been described in detail, it should be understood that various changes, substitutions and alterations can be made therein without departing from the spirit and scope of the invention as defined by the appended claims.

What is claimed is:

1. A combined smoke and gas detector, comprising:

a smoke sensor for sensing the presence of smoke and outputting a smoke level signal indicative of the level of the smoke presence;

a gas detector for sensing the presence of gas and outputting a gas level signal indicative of the level of the gas smoke present, said gas sensor comprising an internal heating element requiring a predetermined amount of time to heat up before accurate gas detection can be made;

smoke detection means for receiving the smoke level signal from said smoke sensor and comparing it with a predetermined smoke threshold and outputting a smoke present signal when the smoke level signal exceeds the smoke threshold;

gas detection means for receiving the gas level signal and comparing it with a predetermined gas threshold and outputting a gas present signal when the gas level signal exceeds the gas threshold;

delay means for delaying the output of said gas detect signal from said gas detection means for a predetermined amount of time to allow said heating element in said gas detector to heat up when the combined smoke and gas detector is activated to prevent a false alarm;

a piezoelectric crystal for providing an audible output tone;

means for modulating said piezoelectric crystal to output a plurality of distinguishable audio output signal, said modulating means turning said piezoelectric crystal on and off at different rates;

a light emitting diode for providing a visual output;

means for controlling said light emitting diode to turn said light emitting diode on and off at a predetermined rate to provide a plurality of distinguishable visual output signals;

means for transmitting said smoke and gas present signals to a remotely disposed smoke and gas detector;

means for receiving a remotely generated gas and smoke present signal from a remotely disposed smoke and gas detector; and control means for receiving said smoke and gas present signals and said remotely generated gas and smoke present signals and controlling said modulating means for said piezoelectric crystal and said light emitting diode to provide a distinguishable audio and visual output for gas present locally alone, smoke present locally alone, combined gas and smoke present locally, remote gas present and remote smoke present, said audio and visual output allowing a user to distinguish between the various combinations of gas present, smoke present, remote gas present and remote smoke present.

2. The combined smoke and gas detector of claim 1 and further comprising test means for testing said smoke sensor.

3. The combined smoke and gas detector of claim 1 and further comprising reset means for disabling the output of said gas detect means for a predetermined amount of time after said control means is output and audible and visual output indicating the presence of gas such that a user can distinguish when one of the gases are present if gas detection is not indicated after said predetermined amount of time.

* * * * *

UNITED STATES PATENT AND TRADEMARK OFFICE
CERTIFICATE OF CORRECTION

PATENT NO. : 4,688,021

DATED : August 18, 1987

INVENTOR(S) : Robert H. Buck, et al.

It is certified that error appears in the above-identified patent and that said Letters Patent is hereby corrected as shown below:

"(73) Assignee: BDC Electronics, Midland, Texas" - delete all reference to Assignee as this patent was not assigned.

Signed and Sealed this

Twenty-first Day of June, 1988

Attest:

DONALD J. QUIGG

Attesting Officer

Commissioner of Patents and Trademarks